United States Patent
Lin et al.

(10) Patent No.: US 11,024,061 B2
(45) Date of Patent: Jun. 1, 2021

(54) APPARATUS AND METHOD FOR SCATTERED RADIATION CORRECTION

(71) Applicant: CARESTREAM HEALTH, INC., Rochester, NY (US)

(72) Inventors: Yuan Lin, Rochester, NY (US); William J. Sehnert, Fairport, NY (US)

(73) Assignee: Carestream Health, Inc., Rochester, NY (US)

(*) Notice: Subject to any disclaimer, the term of this patent is extended or adjusted under 35 U.S.C. 154(b) by 160 days.

(21) Appl. No.: 16/569,771

(22) Filed: Sep. 13, 2019

(65) Prior Publication Data

US 2020/0005496 A1 Jan. 2, 2020

Related U.S. Application Data

(62) Division of application No. 15/012,151, filed on Feb. 1, 2016, now abandoned.
(Continued)

(51) Int. Cl.
*G06T 11/00* (2006.01)
*A61B 6/00* (2006.01)
(Continued)

(52) U.S. Cl.
CPC ............ *G06T 11/005* (2013.01); *A61B 6/022* (2013.01); *A61B 6/025* (2013.01); *A61B 6/032* (2013.01);
(Continued)

(58) Field of Classification Search
None
See application file for complete search history.

(56) References Cited

U.S. PATENT DOCUMENTS 6,256,367 B1  7/2001  Vartanian
6,507,633 B1  1/2003  Elbakri et al.
(Continued)

FOREIGN PATENT DOCUMENTS

DE  102012111385   5/2014
WO  WO 2006/082557  8/2006
WO  WO2016/003957   1/2016

OTHER PUBLICATIONS

Willi A. Kalender et al., "Generating and using combined whole-body patient models for accurate dose estimates in CT: feasibility and validation," Physica Medica: European Journal Medical Physics; Manuscript No. EJMP-D-14-00019, Dec. 2014, 29 pages.
(Continued)

*Primary Examiner* — Michelle M Entezari

(57) ABSTRACT

A method for scattered radiation correction acquires radiographic projection image data for a first portion of a subject that lies within a field of view of an imaging apparatus and characterizes the surface contour of the subject that includes at least a second portion of the subject that lies outside the field of view of the imaging apparatus. The surface contour of the subject is characterized according to the reflectance images. The surface contour characterization is registered to the field of view. Scattered radiation is estimated according to the projection image data and the surface contour characterization. The acquired radiographic projection image data is updated according to the estimated scattered radiation. An image of the field of view is displayed according to the conditioned acquired radiographic projection image data.

16 Claims, 13 Drawing Sheets

Related U.S. Application Data

(60) Provisional application No. 62/244,213, filed on Oct. 21, 2015.

(51) Int. Cl.
  *A61B 6/03* (2006.01)
  *A61B 6/02* (2006.01)
  *G16H 50/50* (2018.01)

(52) U.S. Cl.
  CPC .......... *A61B 6/5282* (2013.01); *G06T 11/008* (2013.01); *G16H 50/50* (2018.01)

(56) References Cited

U.S. PATENT DOCUMENTS

| | | | |
|---|---|---|---|
| 6,958,815 B2 | 10/2005 | Bevilacqua et al. | |
| 8,892,192 B2 | 11/2014 | Cuccia et al. | |
| 8,989,845 B2 | 3/2015 | Brinks et al. | |
| 9,547,940 B1 | 1/2017 | Sun et al. | |
| 9,589,336 B2* | 3/2017 | Flohr | A61B 6/5211 |
| 9,839,404 B2 | 12/2017 | Ruppertshofen et al. | |
| 9,858,663 B2* | 1/2018 | Penney | G06T 15/20 |
| 10,666,928 B2* | 5/2020 | Liu | A61B 90/37 |
| 10,748,296 B2* | 8/2020 | Magro | A61B 5/055 |
| 2004/0058311 A1 | 3/2004 | Fletcher et al. | |
| 2008/0073543 A1 | 3/2008 | Vija et al. | |
| 2008/0095302 A1 | 4/2008 | Ruhrnschopf et al. | |
| 2008/0101657 A1 | 5/2008 | Durkin et al. | |
| 2009/0057560 A1 | 3/2009 | Ray et al. | |
| 2009/0122954 A1 | 5/2009 | Bruder | |
| 2010/0208964 A1 | 8/2010 | Weigert et al. | |
| 2011/0075798 A1 | 3/2011 | Boese et al. | |
| 2011/0080168 A1 | 4/2011 | Fenchel et al. | |
| 2011/0255765 A1 | 10/2011 | Carlson et al. | |
| 2014/0241489 A1* | 8/2014 | Zhang | A61B 6/4275 378/7 |
| 2015/0104092 A1 | 4/2015 | Flohr et al. | |
| 2015/0146952 A1* | 5/2015 | Hashizume | A61B 6/483 382/131 |
| 2015/0313566 A1 | 11/2015 | Diers et al. | |
| 2016/0058401 A1 | 3/2016 | Caruba et al. | |
| 2017/0100088 A1 | 4/2017 | Simon | |

OTHER PUBLICATIONS

Siemens comparison chart, Siemens Computed Tomography (CT) Systems, downloaded May 14, 2018, 1 page.

Gene Ostrovsky, Somatom Definition Flash: All Around Dual Nature CT, Medgadget, May 14, 2018, 5 pages.

HM Helb et al., "Clinical evaluation of simultaneous confocal scanning laser ophthalmoscopy imaging combined with high-resolution, spectral-domain optical coherence tomography," Acta Ophthalmologica, Dec. 1, 2010, 88; pp. 842-849.

* cited by examiner

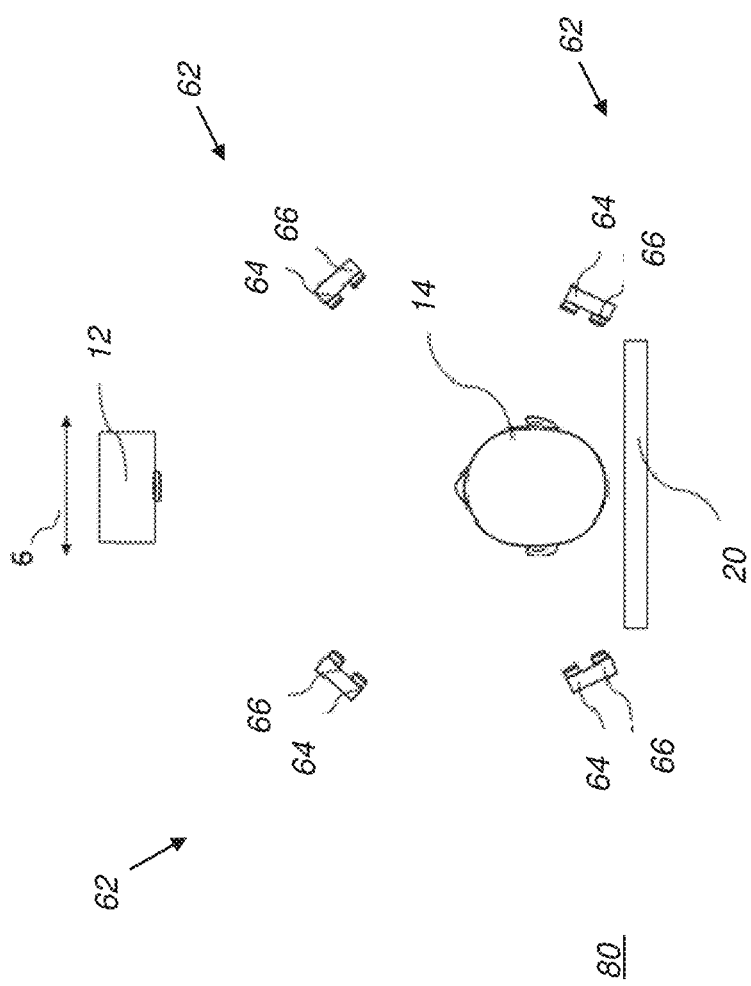

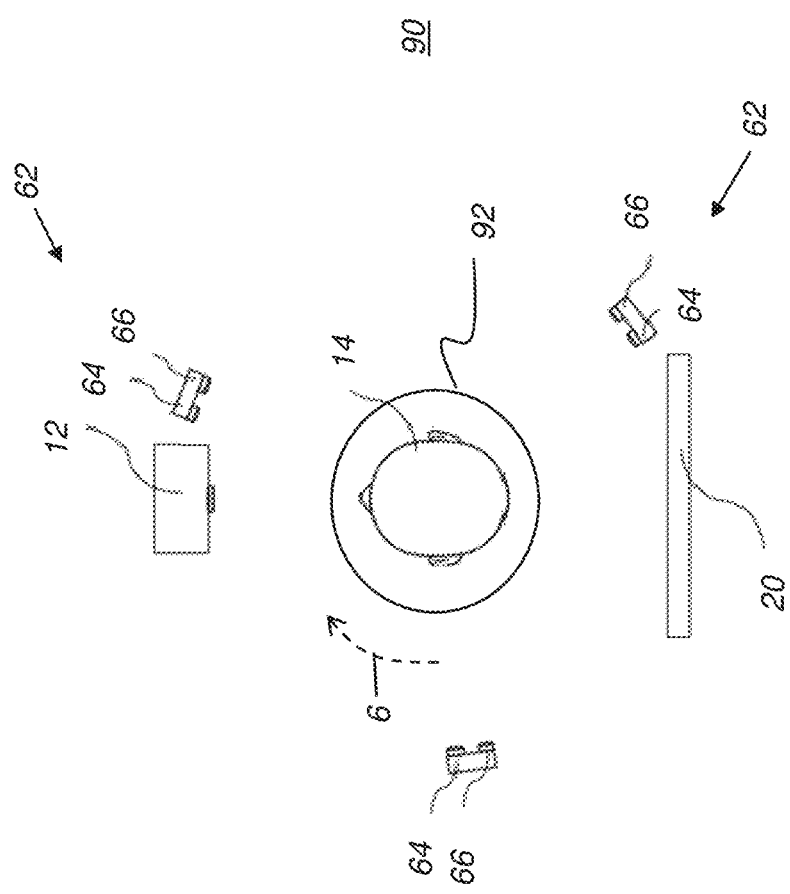

APPARATUS AND METHOD FOR SCATTERED RADIATION CORRECTION

CROSS REFERENCE TO RELATED APPLICATIONS

This application is a divisional patent application of U.S. patent application Ser. No. 15/012,151, filed Feb. 1, 2016, in the name of Lin, et al., entitled APPARATUS AND METHOD FOR SCATTERED RADIATION CORRECTION, which claims the benefit of U.S. Provisional application U.S. Ser. No. 62/244,213, filed on Oct. 21, 2015, entitled "METHOD FOR SCATTERED RADIATION CORRECTION", in the names of Yuan Lin and William J. Sehnert, hereby incorporated by reference herein in its entirety.

TECHNICAL FIELD

The disclosure relates generally to medical imaging and in particular to methods and apparatus for characterization and correction of scatter effects in X-ray images.

BACKGROUND

Various types of X-ray imaging offer useful tools for diagnostic assessment of patient health. Conventional x-ray imaging captures individual, two-dimensional (2D) images of patient anatomy. Volume imaging modalities obtain multiple images in sequence to provide additional depth information, allowing imaging of internal anatomy with three-dimensional (3D) views displayed from different angles and with adjustable sectioning for viewing slices of the volume data, thus allowing the view of internal structures and organs of the patient at different depths from the skin surface.

One known difficulty with X-ray imaging in both 2D imaging modalities (such as radiography, fluoroscopy, or mammography, etc.) and 3D imaging modalities (such as computed tomography CT, multi-detector computed tomography MDCT, cone beam computed tomography CBCT, tomosynthesis, dual energy CT, or spectral CT, etc.) relates to the adverse impact of accumulated effects of scattered radiation on image quality. Scatter itself results from secondary, randomized effects of interaction of the radiation energy with the irradiated tissue. Scatter occurs when radiation from the x-ray source reaches a detector by an indirect path that can extend into material that lies outside the field of view. The primary X-ray beam is directed towards and bombards the sample with some of the X-ray radiation being absorbed, a smaller amount being scattered, and the remainder continuing on to the detector. Scatter is known to contribute to noise and low contrast in the projection images and can substantially reduce image quality and introduce artifacts into the x-ray image or, alternately, into any reconstructed volume images.

Scatter can be modeled probabilistically and compensation for scatter can be applied in the same manner, helping to reduce the effects of scatter on the image content that is acquired. Scatter from the scanned subject can be modeled using information about the X-ray source (such as spectral information, filters, and exposure distribution), about detector response, and also about the materials that lie within the irradiated field of view. Thus, scatter compensation can take advantage of information about the anatomy that receives the radiation. In order to more accurately compensate for scatter, it is further useful to provide ways to model scatter that results from interaction of the radiated energy with materials in the volume that lies outside the field of view.

SUMMARY

Certain embodiments described herein address the need for a method for estimating and compensating for scatter from outside the irradiated field of view. Embodiments of the present disclosure provide methods for modeling the behavior of scattered radiation on tissue that lies within the field of view as well as tissue that lies outside the field of view.

These aspects are given only by way of illustrative example, and such objects may be exemplary of one or more embodiments of the disclosure. Other desirable objectives and advantages inherently achieved by the disclosed disclosure may occur or become apparent to those skilled in the art. The disclosure is defined by the appended claims.

According to an embodiment of the present disclosure, there is provided a method for scattered radiation correction comprising: acquiring radiographic projection image data for a first portion of a subject that lies within a field of view of an imaging apparatus; characterizing a surface contour of the subject, wherein the surface contour includes at least a second portion of the subject that lies outside the field of view of the imaging apparatus; registering the surface contour characterization to the field of view of the acquired projection image data; estimating scattered radiation according to both the acquired projection image data and the surface contour characterization; conditioning the acquired radiographic projection image data according to the estimated scattered radiation; and displaying an image corresponding to the field of view according to the conditioned acquired radiographic projection image data.

BRIEF DESCRIPTION OF THE DRAWINGS

The foregoing and other objects, features, and advantages of the disclosure will be apparent from the following more particular description of the embodiments of the disclosure, as illustrated in the accompanying drawings. The elements of the drawings are not necessarily to scale relative to each other.

FIG. 6D is a schematic top view showing an imaging apparatus for chest tomosynthesis using multiple surface contour acquisition devices placed outside of the imaging system.

FIG. 6E is a schematic top view diagram that shows a computed tomography (CT) imaging apparatus with a rotating subject on a support and with a stationary X-ray source X-ray detector and multiple surface contour acquisition devices.

DETAILED DESCRIPTION OF THE EMBODIMENTS

Figure 1:
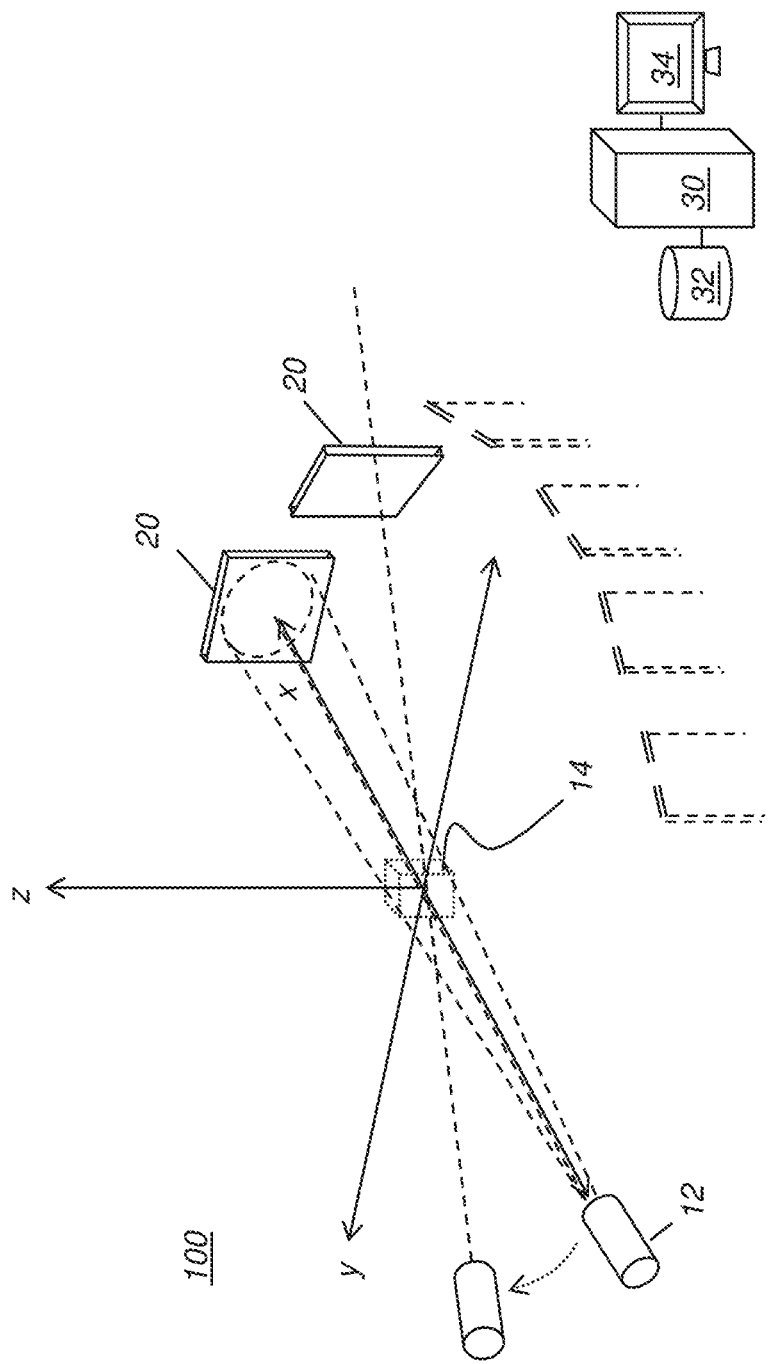
FIG. 1 is a schematic view that shows components of a CBCT image capture and reconstruction system.

The following is a detailed description of the embodiments of the disclosure, reference being made to the drawings in which the same reference numerals identify the same elements of structure in each of the several figures.

Where they are used in the context of the present disclosure, the terms "first", "second", and so on, do not necessarily denote any ordinal, sequential, or priority relation, but are simply used to more clearly distinguish one step, element, or set of elements from another, unless specified otherwise.

As used herein, the term "energizable" relates to a device or set of components that perform an indicated function upon receiving power and, optionally, upon receiving an enabling signal.

In the context of the present disclosure, the phrase "in signal communication" indicates that two or more devices and/or components are capable of communicating with each other via signals that travel over some type of signal path. Signal communication may be wired or wireless. The signals may be communication, power, data, or energy signals. The signal paths may include physical, electrical, magnetic, electromagnetic, optical, wired, and/or wireless connections between the first device and/or component and second device and/or component. The signal paths may also include additional devices and/or components between the first device and/or component and second device and/or component.

In the context of the present disclosure, the term "subject" is used to describe the object that is imaged, such as the "subject patient", for example.

In the context of the present disclosure, "volume image content" describes the reconstructed image data for an imaged subject, generally stored as a set of voxels. Image display utilities use the volume image content in order to display features within the volume, selecting specific voxels that represent the volume content for a particular slice or view of the imaged subject. Thus, volume image content is the body of resource information that is obtained from a CT, CBCT, MDCT, tomosynthesis, or other volume imaging reconstruction process and that can be used to generate depth visualizations of the imaged subject.

To describe an embodiment of the present disclosure in detail, the examples given herein focus on imaging of the human chest and modeling of non-imaged areas of the anatomy lying outside the chest area. However, these examples are considered to be illustrative and non-limiting. Embodiments of the present disclosure can be applied for both 2D imaging modalities, such as radiography, fluoroscopy, or mammography, for example, and 3D imaging modalities, such as CT, MDCT, CBCT, tomosynthesis, dual energy CT, or spectral CT.

In the context of the present disclosure, the term "volume image" is synonymous with the terms "3 dimensional image" or "3D image".

In the context of the present disclosure, a radiographic projection image, more simply termed a "projection image" or "x-ray image", is a 2D image formed from the projection of x-rays through a subject. In conventional radiography, a single projection image of a subject can be obtained and analyzed. In volume imaging such as CT, MDCT, and CBCT imaging, multiple projection images are obtained in series, then processed to combine information from different perspectives in order to form image voxels.

In the context of the present disclosure, the term "surface contour imaging" relates to imaging of the surface of a subject, defining the overall volume of the subject but not defining internal features beneath the skin surface. Surface contour imaging techniques include methods that use reflectance images, such as those obtained from reflectance of visible light or near-infrared light from the surface, as described in more detail subsequently.

Reference is made to US 2011/0255765 (Carlson) titled "Reduction and removal of artifacts from a three-dimensional dental X-ray data set using surface scan information", incorporated by reference herein in its entirety. Reference is further made to US 2010/0208964 (Weigert) titled "Method for Eliminating Scatter Artefacts," and to International Publication WO 2006/082557 entitled "Apparatus and Method for Correction or Extension of X-Ray Projections" by Bertram et al., both incorporated by reference herein in its entirety.

Reference is made to the article "Generating and using combined whole-body patient models for accurate dose estimates in CT: feasibility and validation" by Kalender et al, published in *Physica Medica: European Journal of Medical Physics; Manuscript Number: EJMP-D*-14-00019, incorporated by reference herein in its entirety.

In order to more fully understand the methods of the present disclosure and the problems addressed, it is instructive to review principles and terminology used for CBCT image capture and reconstruction. Referring to the perspective view of FIG. 1, there is shown, in schematic form and using enlarged distances for clarity of description, the activity of a conventional CBCT imaging apparatus 100 for obtaining, from a sequence of 2D radiographic projection images, 2D projection data that are used to reconstruct a 3D volume image of an object or volume of interest, also termed a subject 14 in the context of the present disclosure. Cone-beam radiation source 12 directs a cone of radiation toward subject 14, such as a patient or other subject. For a 3D or volume imaging system, the field of view (FOV) of the imaging apparatus is the subject volume that is defined by the portion of the radiation cone or field that impinges on a detector for each projection image. A sequence of projection images of the field of view is obtained in rapid succession at varying angles about the subject, such as one image at each 1-degree angle increment in a 200-degree orbit. X-ray digital radiation (DR) detector 20 is moved to different imaging positions about subject 14 in concert with corresponding movement of radiation source 12. FIG. 1 shows a representative sampling of DR detector 20 positions to illustrate schematically how projection data are obtained relative to the position of subject 14. Once the needed 2D projection images are captured in this sequence, a suitable imaging algorithm, such as filtered back projection (FBP) or other conventional technique, is used for reconstructing the 3D volume image. Image acquisition and program execution are performed by a computer 30 or by a networked group of computers 30 that are in image data communication with DR detector 20. Image processing and storage is performed using a computer-accessible memory 32. The 3D volume image can be presented on a display 34.

Figure 2:
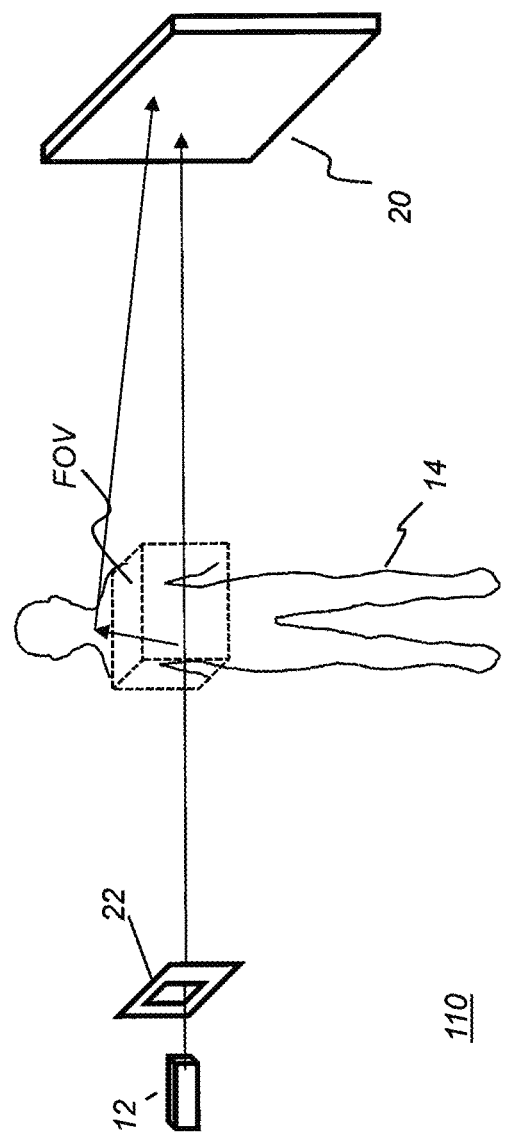
FIG. 2 is a schematic diagram that shows scatter of radiation from portions of the patient outside a field of view.

As shown in FIG. 2, a collimator 22 of a radiography system 110 provides a widely used tool for reducing patient dose. In operation, the collimator helps to direct the emitted radiation from the x-ray source toward a region or field of view (FOV) of the subject, such as a particular body part, over a limited range of angles. Constraining the estimation of scattered radiation to this FOV tends to underestimate the magnitude of the scattered radiation. Some of the radiation, however, scatters and interacts with material that lies outside the field of view, as shown in FIG. 2. This scattered radiation can contribute to scatter that impinges on detector 20, adding substantial unwanted signal to the detected image content.

Using the volume imaging apparatus of FIG. 1, scatter resulting from radiation within the FOV can be estimated and applied to compensate the image content with some accuracy. This is because internal features within the imaged volume can be identified, along with size, density, and other subject-specific information that can affect scatter characteristics. Scatter from outside the FOV, however, as shown in the example of FIG. 2, can be more difficult to characterize. Embodiments of the present disclosure provide methods that can allow more accurate characterization and compensation for scatter from portions of the subject 14 that lie outside the radiation-imaged FOV, such as from adjacent or non-adjacent body parts, to allow improved image quality.

Figure 3:
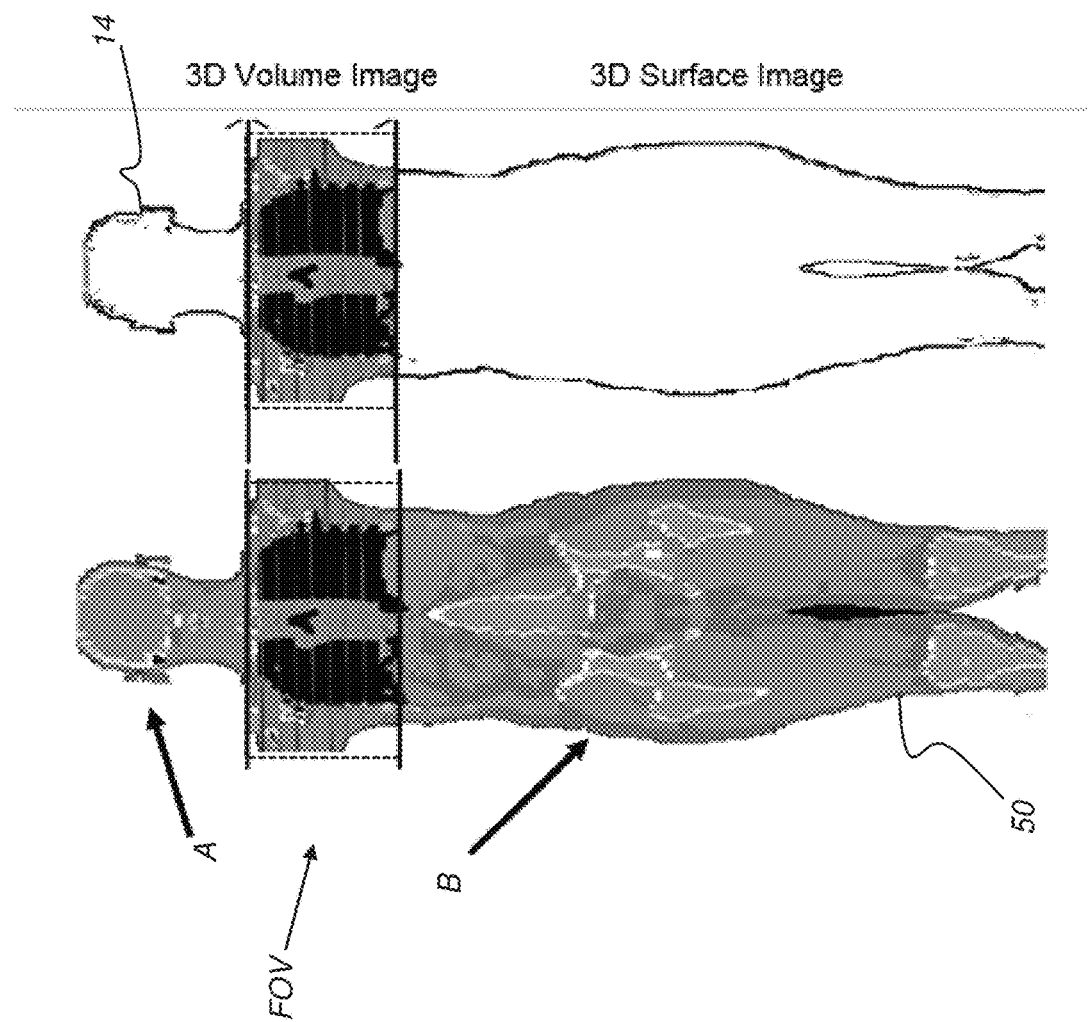
FIG. 3 is a schematic diagram that shows forming an extended volume that includes the field of view and includes other peripheral regions not directly exposed to radiation but contributing to scatter.

FIG. 3 shows schematically features of the modeling that is executed as part of scatter compensation according to an embodiment. For obtaining a chest x-ray of subject 14, the FOV (within the dashed rectangle) is well-defined during the imaging process and the FOV itself is defined by the exposure system collimator. Volumes A and B peripheral to or otherwise outside of the FOV are not well-defined in this manner and some method for determining the effects of scatter from within this outer, peripheral volume can be helpful to more accurately estimate the scattered radiation and to eventually improve the overall diagnostic assessment.

According to at least one embodiment of the present disclosure, an estimate of peripheral volumes A and B of the subject outside of the FOV utilizes volume imaging data that was previously obtained for the patient. The FOV is matched to corresponding volume from previously acquired image data for the patient. A synthetic volume image 50 is then formed, containing volume image data from the most recently scanned projection image content and other volume image content from peripheral volumes of the patient that border the FOV volume of interest. Peripheral volumes can be adjacent to the FOV or from other portions of the patient not directly adjacent to the FOV.

According to an alternate embodiment of the present disclosure, such as when previously scanned volume image data is not available for the patient, volume image data is modeled by determining the volume of the peripheral regions, that is, the volume of the patient lying outside the FOV based on its surface contour, then filling this unradiated volume bounded by the surface contour by assigning an averaged density value to the volume outside the FOV. This forms a synthetic volume image 50 that combines the FOV with peripheral volumes A and B outside the FOV. In some cases, the tissue characteristics of the identified peripheral volume can be approximated using the density and attenuation properties of water or other medium having suitable density to approximate the characteristics. Alternately, a statistically derived standard model or atlas, such as an organ atlas, can be used to model the peripheral volume outside of the FOV. Where this approach is used, data such as height, age, weight, and sex of the patient can be used to select one of a number of different models for determining the volume and features of subject volume outside the FOV based on the acquired surface contour and the reconstructed volume images.

Synthetic volume image 50, combining volume regions outside the FOV with the FOV volume defined according to the surface contour, then serves as a useful mechanism for characterizing and compensating for scatter in the reconstructed image. Areas outside the imaged voxels can thus be used to estimate scatter from outside the FOV to some degree of accuracy. As shown in FIG. 3, this method can provide a fairly accurate model of the subject patient for subsequent computation of scattering.

Surface Contour Acquisition

In order to form synthetic volume image 50, the imaging apparatus needs sufficient data for combining the FOV volume with approximated peripheral volume image information of the subject outside the FOV. To obtain this information, an embodiment of the present disclosure can employ various methods for surface contour acquisition, such as contour acquisition using structured light imaging.

Figure 4:
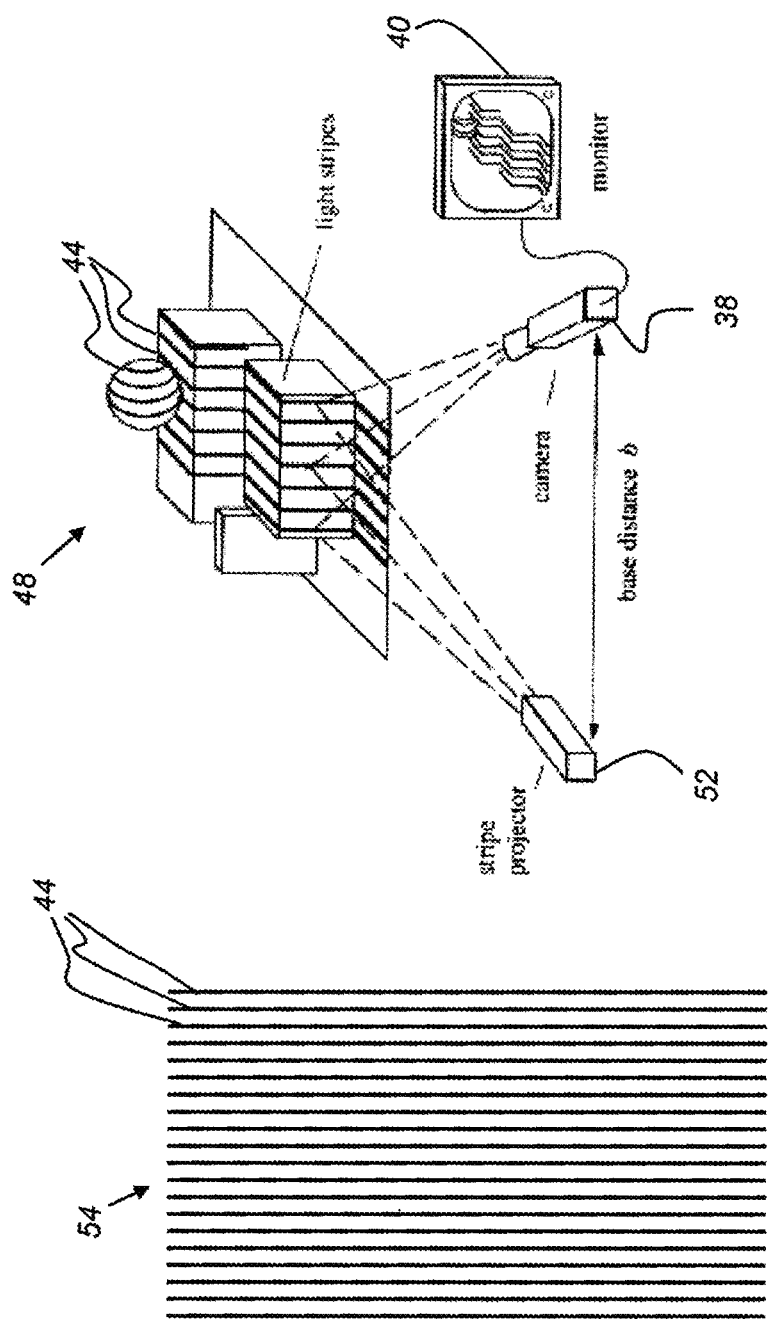
FIG. 4 is a schematic diagram that shows principles and components used for surface contour acquisition using structured light.

FIG. 4 shows surface contour acquisition principles, in schematic form. Surface contour acquisition can be provided from a projector 52 by directing a pattern 54 of lines 44 or other features individually from a laser source at different orbital angles toward a surface 48, represented by multiple geometric shapes. The combined line images, recorded by a camera 38 from different angles but registered to geometric coordinates of the imaging system, provide structured light pattern information. Triangulation principles, using known distances such as base distance b between camera 38 and projector 52, are employed in order to interpret the projected light pattern and compute head and facial contour information from the detected line deviation. Lines 44, or other projected pattern, can be visible light or light of infrared wavelengths not visible to the patient and to the viewer, but visible to the appropriate imaging sensors. An optional monitor 40 shows the acquired surface contour.

Other methods for obtaining the surface contour can alternately be used. Alternate methods familiar to those skilled in the imaging arts include stereovision technique, structure from motion, and time-of-flight techniques, for example. Point data for surface contour characterization can be obtained from numerous devices such as medical scanners using X-Ray or MRI (magneto-resonant imaging); laser range finders (optical, sonar, radar), or vision techniques, such as correlated viewpoints, voxel carving, and stereo range images, for example. The surface imaging apparatus can be hand-held, for example. The surface contour can alternately be expressed as a mesh, using techniques familiar to those skilled in the contour imaging arts.

Figure 5:
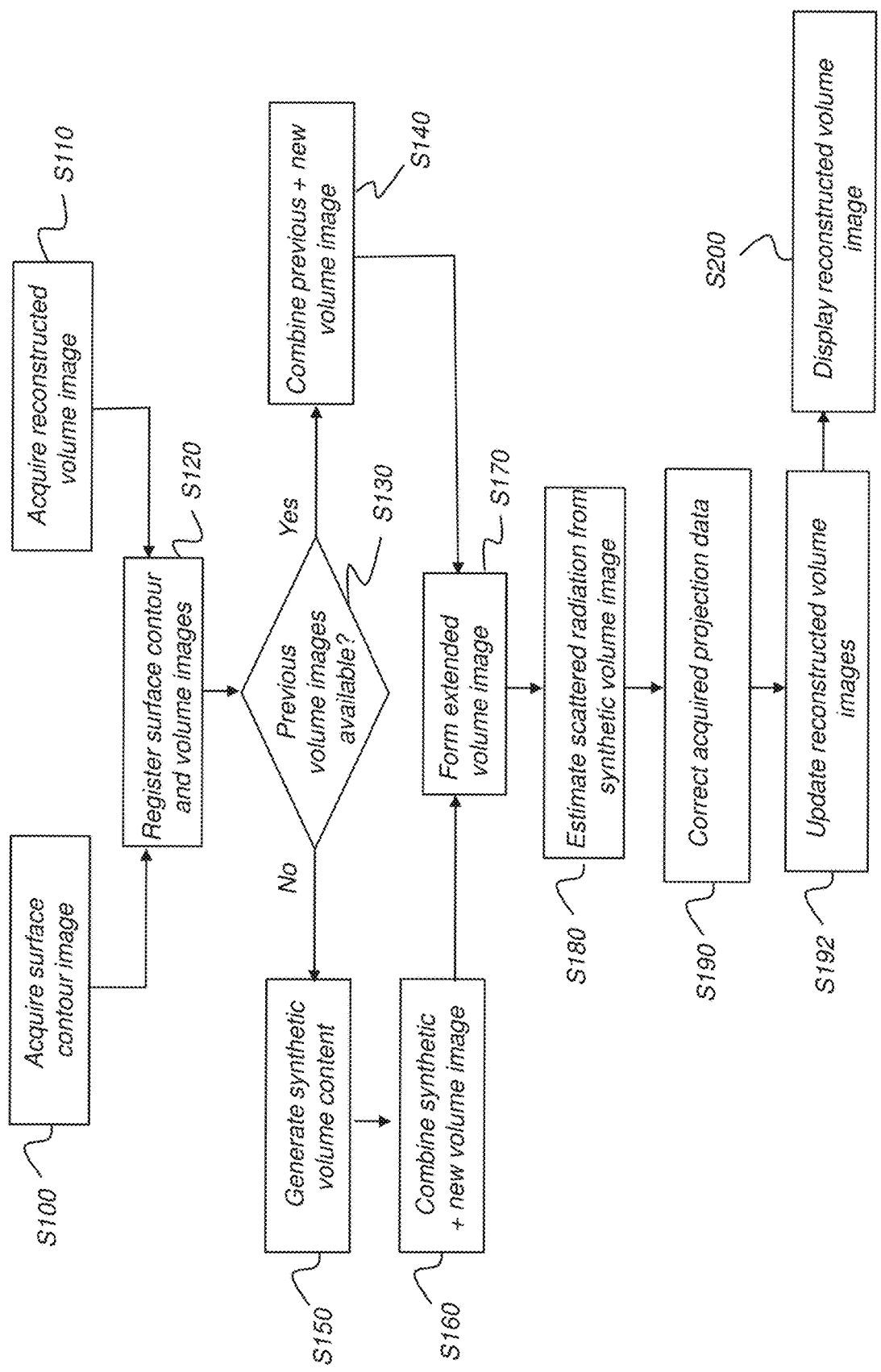
FIG. 5 is a logic flow diagram showing a sequence for scatter estimation and correction according to an embodiment of the present disclosure.

The logic flow diagram of FIG. 5 shows a sequence for scatter estimation and correction according to an embodiment of the present disclosure.

In a surface contour acquisition step S100, surface contour data is acquired, using one of the methods described hereinabove or other suitable method for obtaining surface contour information about a subject. A volume image acquisition step S110, which may execute before or after step S100, acquires volume image data for subject 14 in the FOV that has been reconstructed from 2D projection images, as described previously with respect to FIG. 1. In a registration step S120, the acquired surface contour and volume image content are registered to each other. The volume outside the FOV but lying within the acquired surface contour can now be readily identified and modeled. A decision step S130 then determines, for the imaged subject 14, whether or not previous volume images of the patient are available, based on an earlier CBCT or other radiographic imaging session. Where previous volume image content is available, a combination step S140 executes, in which the FOV data is combined with earlier voxel data. The surface contour information provides guidance on combining the volume content from two different imaging sessions.

Continuing with decision step S130 in FIG. 5, where there is no previous volume image for the patient, a synthetic volume content generation step S150 executes, in which processing models the missing volume content that lies outside the FOV with other volume data. The other volume data can simply be an equivalent volume of water or other material that at least emulates the averaged density of the volume for scatter compensation. Alternately, one or more standardized statistical models can be used. It should be noted that with these methods, the acquired surface contour bounds or defines the volume according to the surface shape. The volume is filled with either a single, uniform material or with a number of different materials and anatomical features, according to the processing in steps S130, S140, and S150. Alternately, the non-imaged volume data can use data interpolated or extended from within the FOV.

Still following the FIG. 5 sequence, in a combination step S160, the new volume image of the FOV and the synthetic volume are combined. A form extended volume image step S170 provides the extended volume image as output, whether the image was obtained using synthetic volume content (steps S150, S160) or using previous images of the patient (step S140). An estimation step S180 then uses the extended volume image of step S170 in order to estimate the scattered radiation. The process of estimating the scattered radiation can use a statistical-based algorithm, such as a Monte-Carlo simulation, or a deterministic-based algorithm, such as a convolution method. By way of reference, Monte Carlo scatter compensation is described, for example, in U.S. Pat. No. 6,256,367 entitled "Monte Carlo Scatter Correction Method for Computed Tomography of General Object Geometries" to Vartanian.

Given the scatter estimate of step S180, projection data is then adjusted for scatter correction in a projection data conditioning step S190. A subsequent update step S192 then updates the reconstruction volume using the corrected projection data. The updated reconstruction volume can be later displayed in a display step S200 as well as stored or transmitted to another computer.

Apparatus for Acquiring Surface Contour and Projection Data

As noted in the logic flow diagram of FIG. 5, both surface contour and volume image content are used for the scatter characterization and correction of the present disclosure. This image content can be acquired from previously stored data that can be from the same imaging apparatus or from different apparatus. However, there can be significant advantages in obtaining the image content from the same apparatus, particularly when executing registration step S120 of FIG. 5. These advantages include the capability to synchronize the processes of surface contour acquisition and volume image acquisition, such as interspersing the timing of image acquisition. This can be particularly useful for reducing motion artifacts, for example, as well as for simplifying registration of the different types of image data.

FIGS. 6A-6E show top view component configurations for a number of different imaging apparatus 10 configurations for acquiring both surface contour and reconstructed volume image data according to embodiments of the present disclosure.

Figure 6A:
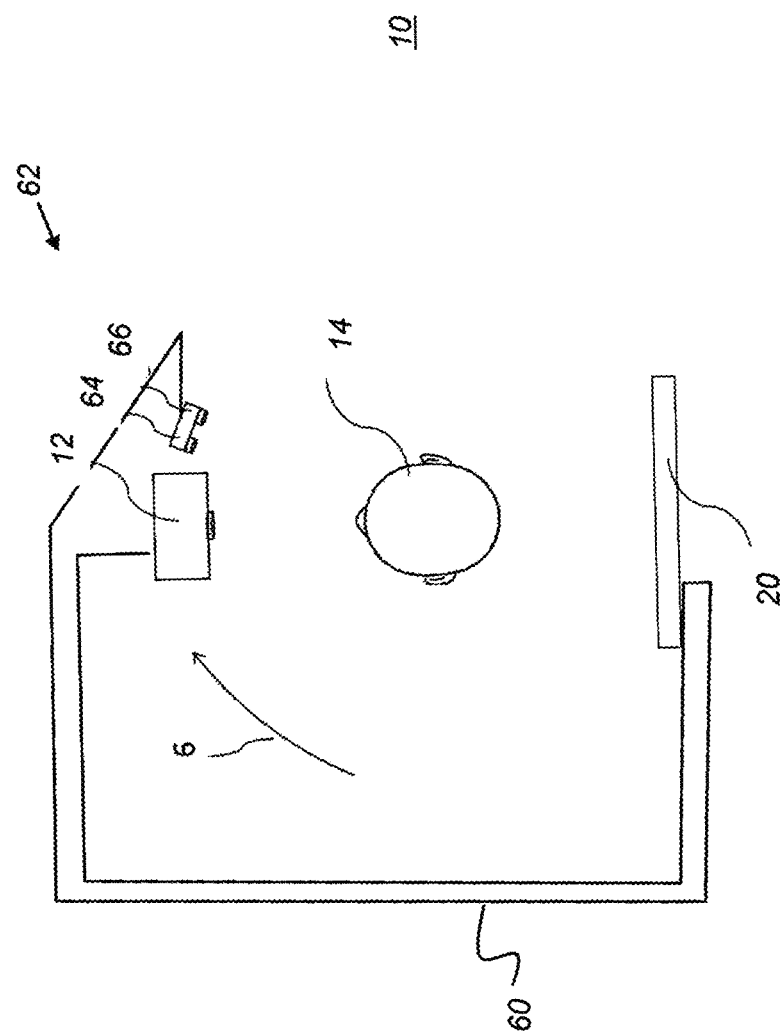
FIG. 6A is a top view schematic diagram of a CBCT imaging apparatus using a rotational gantry for simultaneously acquiring surface contour data using a surface contour acquisition device during projection data acquisition with an X-ray tube and detector.

FIG. 6A shows an arrangement using a rotational gantry 60 that provides a transport apparatus for orbiting x-ray source 12 and detector 20 about subject 14, along with a light scanner 62 having a light pattern projector 64 and a camera or sensor 66. A rotation direction 6 is shown. The FIG. 6A configuration may serve, for example, for a dental imaging device using CBCT combined with structured light imaging.

Figure 6B:
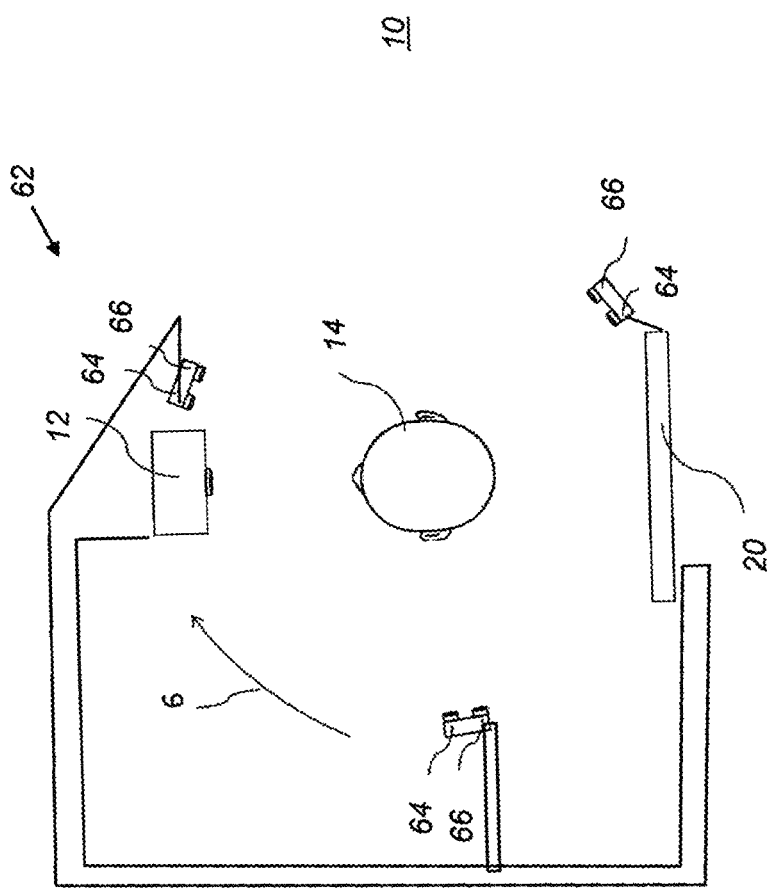
FIG. 6B is a top view schematic diagram of a CBCT imaging apparatus using a rotational gantry for simultaneously acquiring surface contour data using multiple surface contour acquisition devices during projection data acquisition with an X-ray tube and detector.

FIG. 6B shows an arrangement with gantry 60 having x-ray source 12 and detector 20 and a number of pattern projectors 64 and cameras or sensors 66.

Figure 6C:
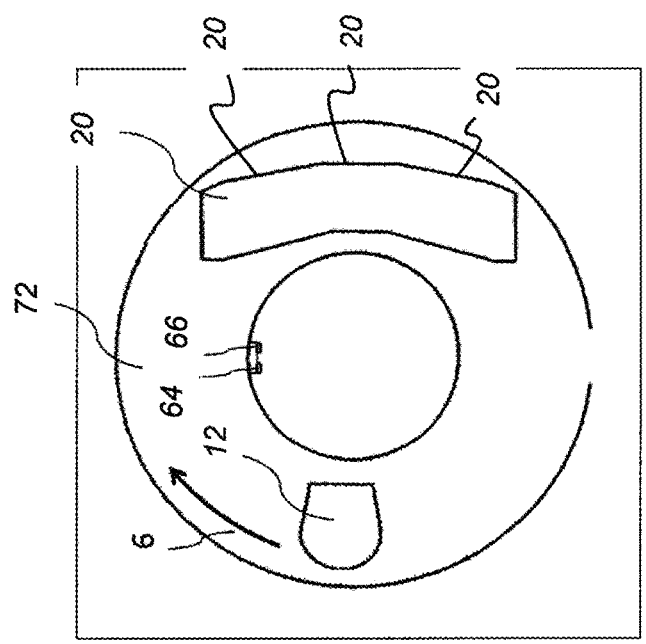
FIG. 6C is a top view schematic diagram of an imaging apparatus for a multi-detector CT (MDCT) system using one surface contour acquisition device affixed to the bore of the MDCT system during projection data acquisition.

FIG. 6C is a schematic diagram showing an MDCT (Multiple-Detector Computed Tomography) apparatus 70 that provides a single x-ray source 12 and a bank of multiple x-ray detectors 20 within a stationary bore 72.

FIG. 6D is a schematic top view showing an imaging apparatus 80 for chest tomosynthesis having multiple pairs of light projectors 64 and sensors 66 external to the x-ray scanner.

FIG. 6E is a schematic top view diagram that shows a computed tomography (CT) imaging apparatus 90 with stationary source 12 and detector 20 and rotating subject 14 on a support 92 that provides a transport apparatus for patient rotation. Stationary scanners 62 for surface contour acquisition are positioned outside the x-ray scanner.

Figure 6F:
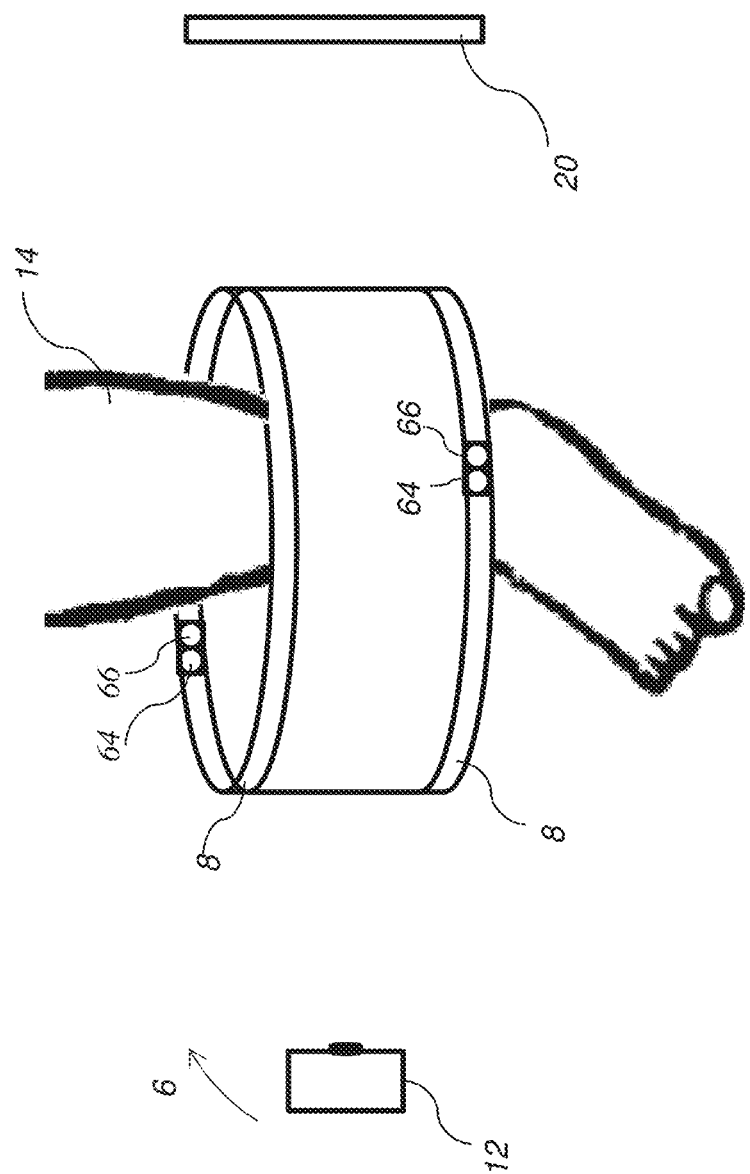
FIG. 6F is a schematic view diagram that shows an extremity X-ray imaging apparatus with multiple surface acquisition devices that can move independently on rails during projection data acquisition.

FIG. 6F is a schematic view diagram that shows an extremity X-ray imaging apparatus for volume imaging, having an x-ray source 12 and detector 20 configured to orbit about subject 14, and having multiple surface contour acquisition devices, scanners 62 that can move independently on rails 8 during projection data acquisition.

Figure 6G:
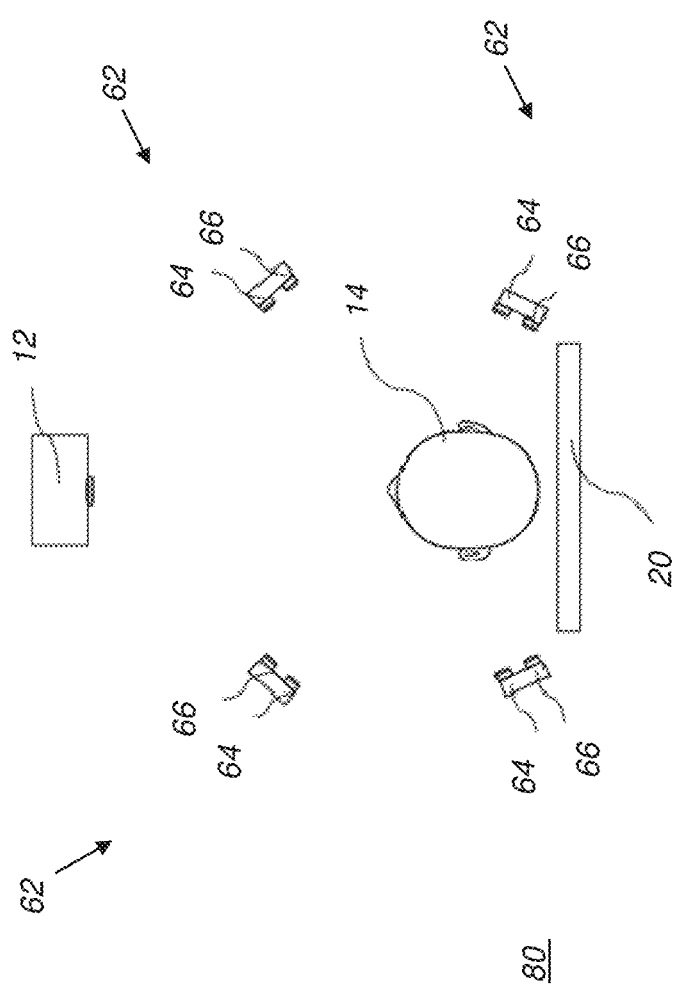
FIG. 6G is a schematic top view showing an imaging apparatus for chest radiographic imaging using multiple surface contour acquisition devices positioned outside of the imaging system.

FIG. 6G is a schematic top view showing imaging apparatus 80 for chest radiographic imaging using multiple scanners 62 to provide multiple surface contour acquisition devices positioned outside of the imaging system.

As described above, embodiments of the present disclosure provide enhanced scatter correction over earlier techniques by using surface contour information to characterize peripheral portions of the subject 14 that lie outside of the system FOV that can contribute to scatter. Earlier methods, for example, do not consider the actual surface contour of the patient but may simply extrapolate typical density values, such as the value for water, to the full peripheral volume that lies outside the FOV when computing the contribution of this peripheral volume to scatter. Because they do not account for the volume of surrounding or peripheral regions, earlier methods may provide an inaccurate model of the surrounding material and incorrectly profile its scattering characteristics for a particular 2D radiographic image or projection image. Embodiments of the present disclosure are directed to providing a more accurate modeling of shape and size characteristics for peripheral volumes, allowing reconstruction of a volume to be more faithful to the original subject 14.

Figure 7:
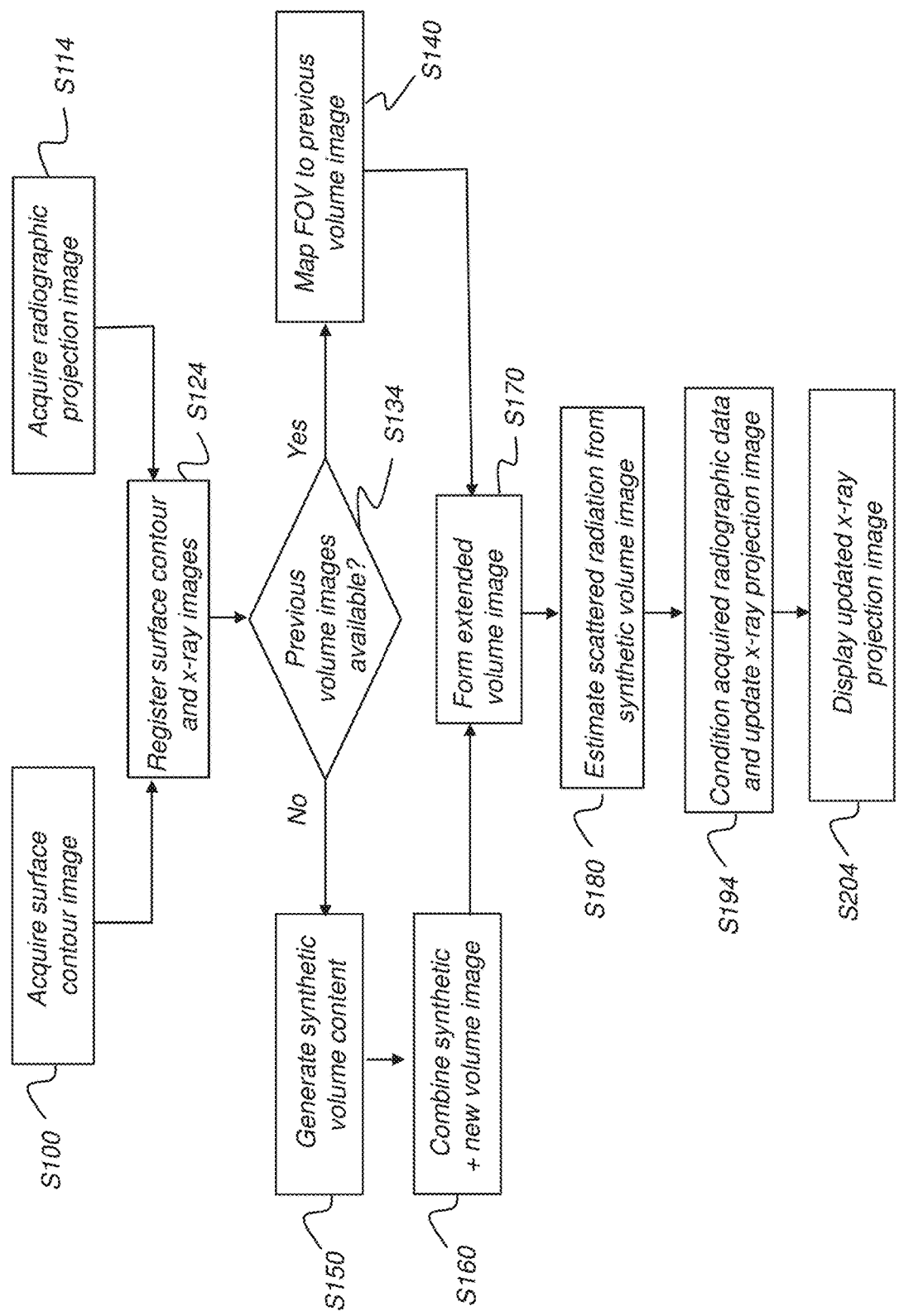
FIG. 7 is a schematic block diagram that shows a sequence for scatter correction for a radiography image.

Embodiments of the present disclosure, while particularly useful for helping to calculate and reduce radiation scatter with 2D projection images that are used for 3D volume image reconstruction, can also be used for scatter correction with projection images obtained in conventional 2D X-ray radiography. The logic flow diagram of FIG. 7 shows a sequence that can be used for scatter correction with radiographic projection images. In surface contour acquisition step S100, surface contour data is acquired, using one of the methods described hereinabove or other suitable method for obtaining surface contour information about a subject 14. The surface contour data that is obtained includes surface contour data associated with the FOV of subject 14 as well as surface contour data for peripheral areas of subject 14 lying outside the FOV. A radiographic image acquisition step S114 obtains the x-ray projection image of the FOV of subject 14 and stores the image content. In a registration step S124, the acquired surface contour and x-ray images are registered to each other. The volume outside the FOV but lying within the acquired surface contour can now be readily identified. A decision step S134 then determines whether or not previous volume images are available, based on an earlier CBCT or other radiographic imaging session. Step S134 may also check for content from a database of images for the individual patient, or from standardized data for a sampling of patients having at least some similar characteristics, such as age, sex, weight, and the like.

Continuing with the process of FIG. 7, where step S134 determines that previous volume image content is not available for use, synthetic volume content generation step S150 executes, in which processing models the missing peripheral volume content that lies outside the FOV with other volume data. The other volume data can simply be an equivalent volume of water or other material that at least emulates the averaged density of the volume for scatter compensation. Alternately, one or more standardized statistical models can be used. It should be noted that with these methods, the acquired surface contour bounds or defines the peripheral volume according to the surface shape. The peripheral volume, associated with the acquired contour, can be filled with either a single, uniform material or with a number of different materials and anatomical features, according to the processing in steps S130, S140, and S150. Alternately, the non-imaged peripheral volume data can use data interpolated or extended from within the FOV.

Still following the FIG. 7 sequence, in combination step S160, the new volume content of the FOV and the synthetic volume are combined. Form extended volume image step S170 provides the extended volume image as output, whether the image was obtained using synthetic volume content (steps S150, S160) or using previous images of the patient (step S140). An estimation step S180 then uses the extended volume image of step S170 in order to estimate the scattered radiation. The process of estimating the scattered radiation can use a statistical-based algorithm, such as a Monte-Carlo simulation, or a deterministic-based algorithm, such as a convolution method.

Given the scatter estimate of step S180, radiographic data can then be adjusted for scatter correction in a condition acquired radiographic data step S194. Condition acquired radiographic data step S194 then updates the radiographic projection image using the corrected radiographic data. The updated x-ray projection image can be later displayed in a display step S204 as well as stored or transmitted to another computer.

It can be appreciated that other processing sequences can alternately be executed using the combined contour image and projection image data to calculate scatter as described herein. A database of volume image content for patients of similar build and other characteristics can be combined with surface contour data to generate a scatter model that more closely approximates scatter conditions than do methods that simply assign default characteristics to tissue regions outside of the FOV and coarsely estimate their contribution to scatter effects.

Consistent with at least one embodiment, the present disclosure utilizes a computer program with stored instructions that control system functions for image acquisition and image data processing for image data that is stored and accessed from an electronic memory. As can be appreciated by those skilled in the image processing arts, a computer program of an embodiment of the present disclosure can be utilized by a suitable, general-purpose computer system, such as a personal computer or workstation that acts as an image processor, when provided with a suitable software program so that the processor operates to acquire, process, transmit, store, and display data as described herein. Many other types of computer systems architectures can be used to execute the computer program of the present disclosure, including an arrangement of networked processors, for example.

The computer program for performing the method of the present disclosure may be stored in a computer readable storage medium. This medium may comprise, for example; magnetic storage media such as a magnetic disk such as a hard drive or removable device or magnetic tape; optical storage media such as an optical disc, optical tape, or machine readable optical encoding; solid state electronic storage devices such as random access memory (RAM), or read only memory (ROM); or any other physical device or medium employed to store a computer program. The computer program for performing the method of the present disclosure may also be stored on computer readable storage medium that is connected to the image processor by way of the internet or other network or communication medium. Those skilled in the image data processing arts will further readily recognize that the equivalent of such a computer program product may also be constructed in hardware.

It is noted that the term "memory", equivalent to "computer-accessible memory" in the context of the present disclosure, can refer to any type of temporary or more enduring data storage workspace used for storing and operating upon image data and accessible to a computer system, including a database. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer can also be considered to be a memory, as the term is used in the present disclosure. Memory is also used as the data workspace for executing and storing intermediate and final results of calculations and other processing. Computer-accessible memory can be volatile, non-volatile, or a hybrid combination of volatile and non-volatile types.

It is understood that the computer program product of the present disclosure may make use of various image manipulation algorithms and processes that are well known. It will be further understood that the computer program product embodiment of the present disclosure may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product of the present disclosure, are not specifically shown or described herein and may be selected from such algorithms, systems, hardware, components and elements known in the art.

The disclosure has been described in detail, and may have been described with particular reference to a suitable or presently preferred embodiment, but it will be understood that variations and modifications can be effected within the spirit and scope of the disclosure. The presently disclosed embodiments are therefore considered in all respects to be illustrative and not restrictive. The scope of the disclosure is indicated by the appended claims, and all changes that come within the meaning and range of equivalents thereof are intended to be embraced therein.

What is claimed is:

1. A scattered X-ray radiation correction method for 2D X-ray imaging, the method comprising the steps of:
    acquiring X-ray projection data for an X-ray image of a subject within a field of view of a digital X-ray radiation detector;
    acquiring surface contour data of a portion of the subject within the field of view of the digital X-ray radiation detector and acquiring surface contour data of the subject outside the field of view of the digital X-ray radiation detector;
    registering the acquired surface contour data of the subject to the acquired X-ray projection data of the subject;
    estimating scattered X-ray radiation effects within the acquired X-ray projection data of the subject caused by X-ray radiation scattered by a portion of the subject that lies outside the field of view of the digital X-ray radiation detector and which impacts the digital X-ray radiation detector; and
    correcting the acquired X-ray projection data of the subject according to the estimated scattered X-ray radiation effects therewithin.

2. The method of claim 1, further comprising generating an extended X-ray image of the subject, including adding to the acquired surface contour data additional data defining one of a single uniform material, or a plurality of materials with anatomical structures.

3. The method of claim 1, further comprising generating an extended X-ray image of the subject, including adding a plurality of materials with anatomical structures obtained from the acquired X-ray projection data, an organ atlas, or one or more medical images stored in a database.

4. The method of claim 3, further comprising cropping, deforming, resizing, stretching, rotating, or reorganizing anatomical structures of the one or more medical images stored in the database to match the extended X-ray image of the subject.

5. The method of claim 1, further comprising generating an extended X-ray image of the subject, including cropping, deforming, resizing, stretching, rotating, or reorganizing anatomical structures of medical images stored in a database to match the acquired surface contour data.

6. The method of claim 1, wherein estimating the scattered radiation comprises using a statistical-based algorithm or a deterministic-based algorithm.

7. The method of claim 1, wherein the corrected projection data is displayed on a monitor or stored to a disk.

8. The method of claim 1, wherein the step of acquiring the surface contour data of a portion of the subject within and outside the field of view of the digital X-ray radiation detector comprises acquiring a plurality of reflectance images of the subject.

9. The method of claim 8, wherein acquiring the plurality of reflectance images of the subject comprises recording reflections of a pattern of visible light that is directed onto the subject.

10. The method of claim 1, wherein the step of acquiring the X-ray projection data of the subject comprises acquiring a plurality of X-ray projection images of the subject each at a different angle with respect to the subject.

11. The method of claim 10, further comprising forming a reconstructed volume image of the subject from the acquired plurality of X-ray projection images of the subject.

12. The method of claim 10, wherein the step of correcting the acquired X-ray projection data of the subject comprises correcting the plurality of X-ray projection images of the subject according to the estimated scattered X-ray radiation effects within the acquired X-ray projection data of the subject.

13. The method of claim 12, further comprising forming a corrected reconstructed volume image of the subject from the corrected plurality of X-ray projection images of the subject.

14. The method of claim 8, wherein acquiring the plurality of reflectance images comprises using one or more surface imaging apparatus mounted to a rotational gantry of an x-ray imaging system.

15. The method of claim 1, wherein the step of acquiring surface contour data of a portion of the subject comprises using a reflectance imaging apparatus coupled to an imaging bore of an x-ray imaging system.

16. The method of claim 1, wherein the step of acquiring surface contour data of a portion of the subject comprises using one of a stereovision technique, a structured light technique, a structure from motion technique, and a time-of-flight technique.

* * * * *